United States Patent
Zilla et al.

(10) Patent No.: US 8,702,782 B2
(45) Date of Patent: Apr. 22, 2014

(54) STENT DEPLOYMENT DEVICE

(75) Inventors: Peter Paul Zilla, Cape Town (ZA); Deon Bezuidenhout, Cape Town (ZA); David Franklyn Williams, Brussels (BE)

(73) Assignee: Strait Access Technologies Holdings (Pty) Limited, Observatory (ZA)

( * ) Notice: Subject to any disclaimer, the term of this patent is extended or adjusted under 35 U.S.C. 154(b) by 210 days.

(21) Appl. No.: 13/123,380

(22) PCT Filed: Oct. 8, 2009

(86) PCT No.: PCT/IB2009/007063
§ 371 (c)(1),
(2), (4) Date: May 13, 2011

(87) PCT Pub. No.: WO2010/041125
PCT Pub. Date: Apr. 15, 2010

(65) Prior Publication Data
US 2012/0059447 A1 Mar. 8, 2012

Related U.S. Application Data (60) Provisional application No. 61/104,006, filed on Oct. 9, 2008.

(51) Int. Cl.
*A61F 2/06* (2013.01)
(52) U.S. Cl.
USPC ........................................................ 623/1.11
(58) Field of Classification Search
USPC ............ 623/1.11, 1.12, 2.11, 1.24, 1.25, 1.26
See application file for complete search history.

(56) References Cited

U.S. PATENT DOCUMENTS

| | | | |
|---|---|---|---|
| 4,655,771 | A | 4/1987 | Wallsten |
| 4,661,094 | A | 4/1987 | Simpson |
| 4,790,315 | A | 12/1988 | Mueller, Jr. et al. |

(Continued)

FOREIGN PATENT DOCUMENTS

| | | |
|---|---|---|
| CN | 201008562 | 1/2008 |
| WO | 2009/108942 | 9/2009 |

OTHER PUBLICATIONS

A. Holzmann, Written Opinion of the International Searching Authority in PCT/IB2009/007063, Mar. 16, 2010, Austrian Patent Office, Vienna, Austria.

(Continued)

*Primary Examiner* — Thomas McEvoy
(74) *Attorney, Agent, or Firm* — Florek & Endres PLLC (57) ABSTRACT

A stent deployment device over which a stent is securable for the purpose of delivery into an operative position in a human body is provided. The device comprises a plurality of elongate wings, each of which has a length consistent with the length of a stent to be deployed using the deployment device, the wings being arranged circumferentially about a central body which extends from, and is operable through, a catheter. The wings are movable between a radially withdrawn delivery position and expanded positions in which they are displaced radially outwards of the body. A flow path is defined internally of the wings in the expanded positions thereof and a temporary valve is provided in such flow path to permit the flow of blood though the flow path predominantly in one direction. An inflatable annular balloon is preferably provided over the wings to cause final expansion of the stent. Locator arms are deployable from the body to assist in locating the body within a natural heart valve.

13 Claims, 5 Drawing Sheets

(56) References Cited

U.S. PATENT DOCUMENTS

| | | | |
|---|---|---|---|
| 4,909,252 | A | 3/1990 | Goldberger |
| 5,158,540 | A | 10/1992 | Wijay et al. |
| 5,332,402 | A | 7/1994 | Teitelbaum |
| 5,370,617 | A | 12/1994 | Sahota |
| 5,397,351 | A | 3/1995 | Pavcnik et al. |
| 5,554,185 | A | 9/1996 | Block et al. |
| 5,618,300 | A | 4/1997 | Marin et al. |
| 5,855,565 | A | 1/1999 | Bar-Cohen et al. |
| 5,855,601 | A | 1/1999 | Bessler et al. |
| 5,957,949 | A | 9/1999 | Leonhardt et al. |
| 6,007,517 | A | 12/1999 | Anderson |
| 6,458,153 | B1 | 10/2002 | Bailey et al. |
| 6,530,952 | B2 | 3/2003 | Vesely |
| 2004/0225354 | A1 | 11/2004 | Allen et al. |
| 2006/0020332 | A1 | 1/2006 | Lashinski et al. |
| 2008/0228254 | A1* | 9/2008 | Ryan ............... 623/1.2 |
| 2010/0004739 | A1* | 1/2010 | Vesely .......... 623/2.11 |

OTHER PUBLICATIONS

A. Holzmann, International Search Report in PCT/IB2009/007063, Mar. 16, 2010, Austrian Patent Office, Vienna, Austria.

Chinese Patent Office; Notification of the First Office Action in Chinese Application No. 200980140389.7; Apr. 3, 2013; 12 pages (7 page English translation; 5 page original Chinese), The State Intellectual Property Office of the People's Republic of China; China.

\* cited by examiner

STENT DEPLOYMENT DEVICE

This application is a U.S. National Stage filing under 35 U.S.C. §371 of International Application No. PCT/IB2009/007063, filed Oct. 8, 2009, which in turn claims priority to U.S. Provisional Application Ser. No. 61/104,006, filed Oct. 9, 2008.

FIELD OF THE INVENTION

This invention relates to a device for deploying a stent in a human body. More particularly, but not exclusively, it relates to a device for deploying a stent carrying a prosthetic replacement heart valve or an endovascular graft.

BACKGROUND TO THE INVENTION

Diseased heart valves often malfunction and this may eventually lead to heart failure and death. It is estimated that between 275,000 and 370,000 valve replacements are being performed each year.

The majority of these are done in the USA, Europe and Japan where access to cardiac surgery is widely available. In the developing world, patients often have no access to open heart surgery due to the absence of a heart lung machine. A procedure that does not require a heart lung machine, whilst being beneficial for certain groups in the developed world, is essentially the only option for the millions in the developing world.

Catheter-based endovascular procedures have been developed in which a catheter is inserted through a peripheral blood vessel or closed chambers of the heart. The method of choice for both the dilatation of stenotic valves and the expansion of crimped stent-mounted valves is balloon inflation. However, although ballooning of mitral valves has become a routine procedure over the past two decades, balloon obstruction of the aortic valve creates a very different situation. The obstruction of an inflow valve such as the mitral valve during the contraction of the heart (systole) does not limit the ability of the heart muscle to eject the blood, but obstruction of the aortic valve prevents the left heart chamber from emptying its contents. This isometric contraction leads to the generation of supra-systolic pressures which not only bear a high risk of valve dislodgement but also lead to overstraining of the heart muscle.

In order to overcome the dangers and complications associated with outflow obstruction during the balloon inflation, highly sophisticated approaches have been developed. To significantly reduce cardiac ejection during the procedure, rapid right ventricular pacing may be performed prior to inflation. The balloon then needs to be immediately inflated, deflated and withdrawn from the outflow tract.

Two or three balloon inflations are normally performed for effective predilatation of the replacement valve. Using the calcification of the native valve and a reference image obtained during supra-aortic angiography as markers, as well as sophisticated intra- and extra cardiac sonography, the centre of the catheter-mounted replacement valve may be accurately positioned in the middle of the native valve. Immediately prior to delivery, rapid pacing is again induced and the balloon is instantly inflated with contrast medium. After complete expansion, the balloon must be immediately deflated and the rapid pacing interrupted. The total duration of rapid pacing and balloon inflation should not exceed a few seconds.

Given the obstructive nature of expansion balloons, self-expanding valve stents made of shape memory alloys have been introduced. As their clinical success remains to be proven, pre-dilatation of the stenotic valve still requires a balloon. A variety of self-expanding valves has been reported ranging from the utilization of shape memory materials such as Nitinol to inflatable valve stents (U.S. Pat. Nos. 5,554,185; 4,655,771; 5,332,402; 5,397,351; 5,855,601; and 5,957,949 describe such valve stents.

Generally, deployment and/or dilatation devices share the problem of flow-occlusion during expansion. One proposed solution to maintain blood flow is based on rigid tubular structures providing a communication between the up-stream and down-stream lumen. (U.S. Pat. Nos. 4,661,094 and 4,790,315).

U.S. Pat. No. 5,158,540 discloses a motorized pump in a double-balloon design to increase the perfusion flow. U.S. Pat. No. 5,370,617 additionally discloses the use of the guide wire lumen after withdrawal of the guide wire to add luminal perfusion capacity.

Alternatively, the balloon component of dilatation/deployment catheters or devices can be replaced by a mechanical dilatation mechanism. In consequence, device expansion is not associated with obstructive occlusion of blood flow. However, this arrangement is not suitable for use with heart valve replacements as flow is permitted in both directions and thus the heart will not be able to pump blood during deployment.

Recognizing the importance of a balloon-based expansion system for both stenotic valvular lesions and non self-expanding stents, various inventions have dealt with overcoming blood flow obstruction. U.S. Pat. No. 6,458,153 discloses channels or ridges at the outside of the balloons to permit blood flow.

U.S. Pat. No. 6,007,517 describes an angioplasty balloon for coronary interventions with one or more asymmetrically positioned longitudinal channels aiming at the maintenance of blood flow through the expanded balloon.

Goldberger (U.S. Pat. No. 4,909,252) describes a donut-shaped balloon with a double-walled bladder, providing a central orifice. The invention is claimed for valvuloplasty but not stented valve expansion against calcific stenosis, as deliverable pressures may be insufficient.

Due to the scantiness of delivery systems making provision for sufficient blood-flow during the inflation of an expansion balloon, the issue of a need for biased flow direction has hardly been addressed heretofore.

Vesely (U.S. Pat. No. 6,530,952) describes a delivery system for an endovascular valve placement and replacement system that includes a 'surgical platform' anchoring the numerous catheters and devices in space, thereby ensuring proper controlled manipulation. An integrated check valve within this surgical platform would enable controlled ejection of blood from the ventricle during valve placement or removal. Its location distal from the replacement valve brings the coronary ostia onto the wrong side of the check valve, preventing blood filling of the coronary arteries from the aorta during diastole. Similar shortcomings can be ascribed to the Medtronic invention of a temporary heart valve in the ascending aorta (Allen US patent application 2004/0225354). A similar principle underlies the Lashinski patent application (US 2006/0020332).

OBJECT OF THE INVENTION

It is an object of this invention to provide a stent deployment device which at least partially alleviates some of the abovementioned problems.

SUMMARY OF THE INVENTION

In accordance with this invention there is provided a stent deployment device over which a stent is securable for the purpose of delivery into an operative position in a human body, the device comprising a plurality of elongate wings, each of which has a length consistent with the length of a stent to be deployed using the deployment device, wherein the wings are arranged circumferentially about a central body which extends from, and is operable through, a catheter; the wings being movable between a radially withdrawn delivery position and expanded positions in which they are displaced radially outwards of the body; expansion means that are operable with sufficient force to cause at least partial expansion of a stent carried by the device during movement of the wings from the delivery position to an expanded position, and wherein a flow path is defined internally of the wings in the expanded positions thereof, the device being characterized in that a temporary valve is provided in such flow path to permit flow of blood though the flow path predominantly in one direction.

Further features of the invention provide for an annular expansion balloon to be provided over the wings the expansion balloon being inflatable to expand circumferentially to cause a second phase of expansion of a stent carried on the device; for a number of elongate locator arms to be secured to the body and deployable from a stowed condition on the body to engage within a heart valve to locate the body within the heart valve; for the locator arms to be curved in their length and flexible with respect to the body; and for the locator arms to be hingedly secured to the body at or near one end thereof.

Still further features of the invention provide for the flow path to the defined in part by a membrane spanning the wings; and for the membrane to be tubular and to carry the temporary valve internally thereof.

Yet further features of the invention provide for the expansion means to include struts that are operable between a stowed condition in which they extend generally in the direction of the length of the body, and an extended condition in which they extend in a generally more radial direction from the body; for the struts to be pivotally attached to the body intermediate their ends, to the wings at one extremity of each strut, and to an axially movable sleeve internally of the body at the other extremity of each strut; and alternatively, for the struts to be operable to expand in a generally radial direction from the body.

The invention also provides a stent deployment device as defined above wherein a stent is pre-crimped over the wings and, where appropriate, annular expansion balloon, with the wings in a radially withdrawn delivery position. The stent may support a replacement heart valve or an endovascular graft.

Of course, the expansion means do not need to include struts and it is within the scope of this invention that other mechanical means can be employed to move the wings outwards from the delivery position to an expanded position as well as pneumatically or hydraulically operated expansion means.

Further features of the invention provide for the wings to have a curved outer surface adjacent the stent; and for some of the wings to be longer than others to extend past one end of the stent.

DETAILED DESCRIPTION WITH REFERENCE TO THE DRAWINGS

Figure 1:
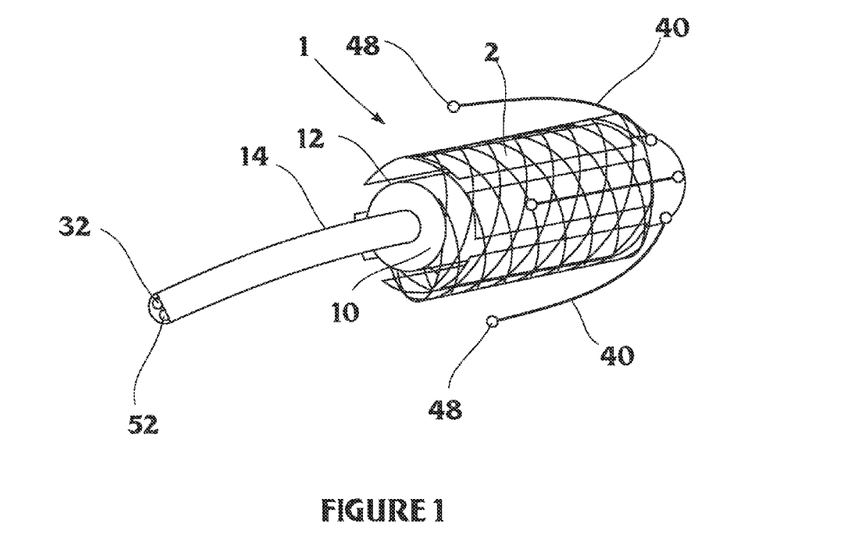
FIG. 1 is a schematic perspective view of a stent deployment device with a stent secured thereover.
Figure 2:
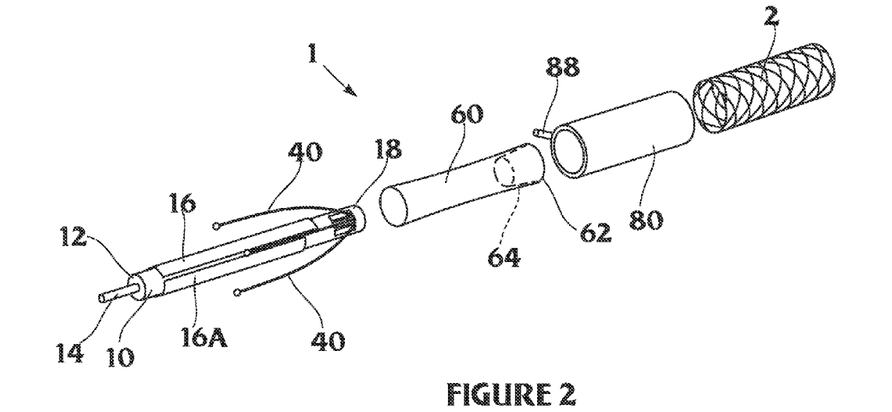
FIG. 2 is an exploded perspective view of the stent deployment device illustrated in FIG. 1.

A stent deployment device (1) is shown in FIGS. 1 and 2 with a stent (2) secured thereon. The stent (2) is of the conventional heart replacement type and need not be described any further except to indicate that it is essentially a metal tube having a set of shaped holes formed therein to give it a meshed appearance and has leaflets of a replacement valve (not shown) secured internally thereof. Typically the shaped holes are of a diamond shape. The stent is secured over the stent deployment device (1) by crimping it thereon preparatory to deployment.

The deployment device (1) includes an elongate body (10) having a cylindrical shape and which is secured at one end (12) to a catheter (14). Referring also to FIGS. 3 to 6, the body (10) has, in this embodiment, six elongate wings (16) located about its outer surface. The wings are elongate plate-like elements which are somewhat curved in their width such that when arranged side by side on the body (10) they provide a circular cylindrical circumference. The wings (16) extend from adjacent the end (12) of the body (10) along its length but terminate short of the opposite end (18) of the body. Also, alternate wings (16A) are slightly shorter than the remainder for a reason which will become more apparent below. The wings (16A) are, in this embodiment of the invention, at least the same length as the stent (2) and the remaining wings are slightly longer. The outer surfaces of the wings define support surfaces for the stent.

Figure 3:
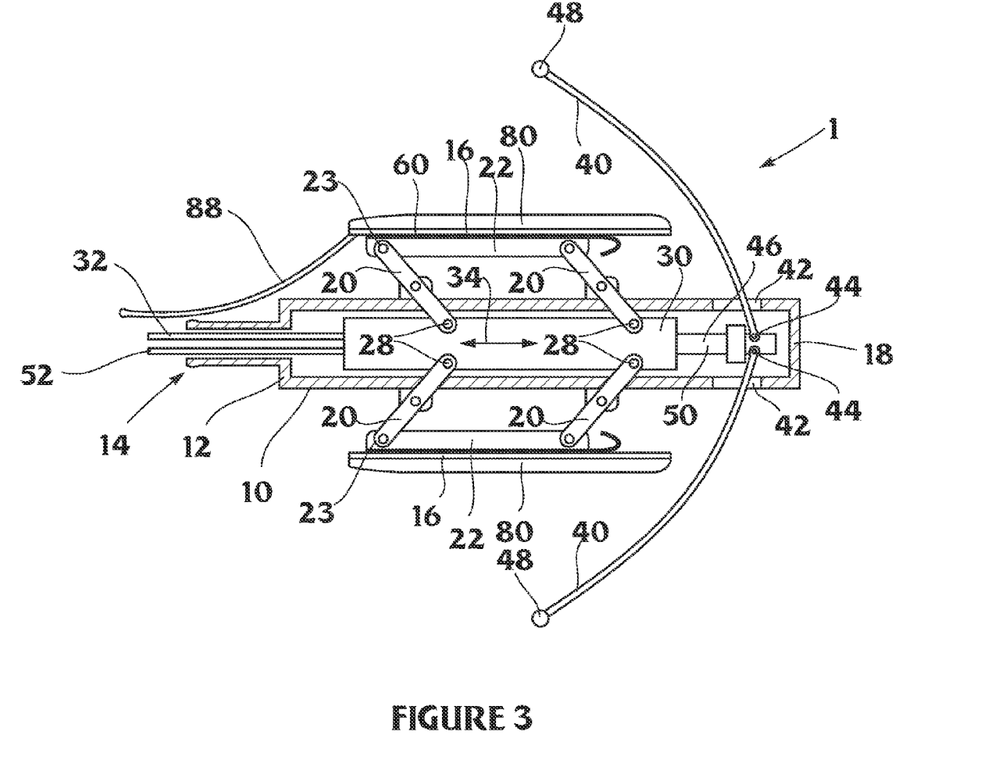
FIG. 3 is a sectional side elevation of the stent deployment device in illustrated FIG. 1.
Figure 3A:
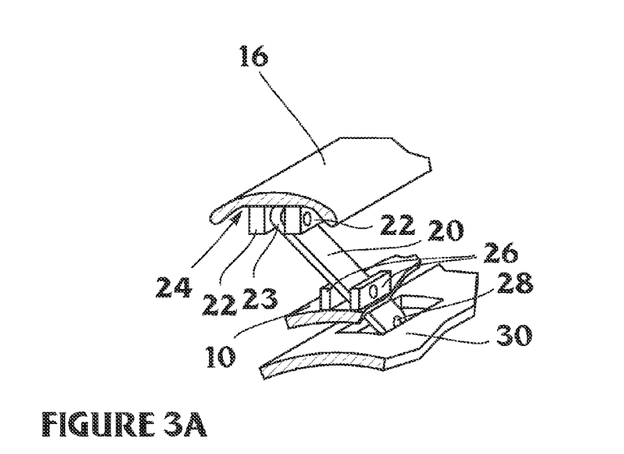
FIG. 3A is a detail of the strut attachment illustrated in FIG. 3.

The wings (16) are each secured to the body (10) through a pair of struts (20). Each strut (20) is hingedly secured at one end thereof between a pair of rails (22) extending normally from the inner side (24) of each wing (16) and centrally thereof. Each strut (20) is also hingedly secured partway along its length between a pair of lugs on the body (10) to form a central hinge (26). The other end (28) of each strut (20) is in turn received in an elongate aperture (not shown) in a sleeve (30) slidable axially within the body (10) and operable through a cable (32) running within the catheter (14). Operation of the cable (32) causes the sleeve (30) to move axially within the body (10), as indicated by arrow (34).

Figure 4:
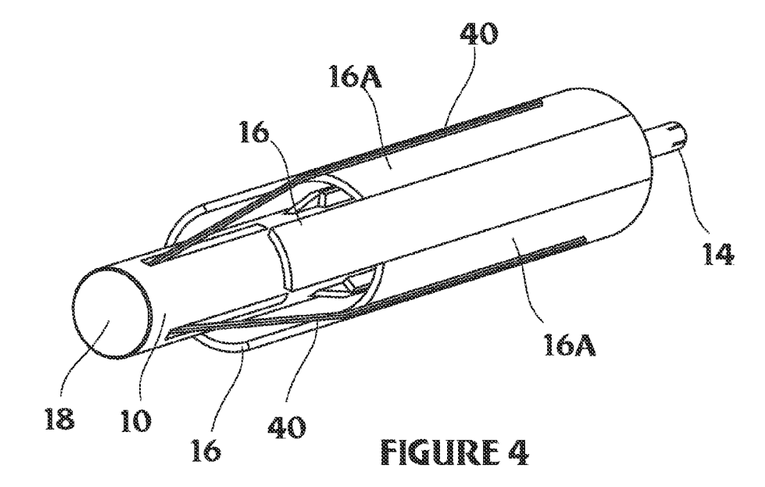
FIG. 4 is a further perspective view of the body of the stent deployment device illustrated in FIG. 1 with the wings in a delivery position.
Figure 5:
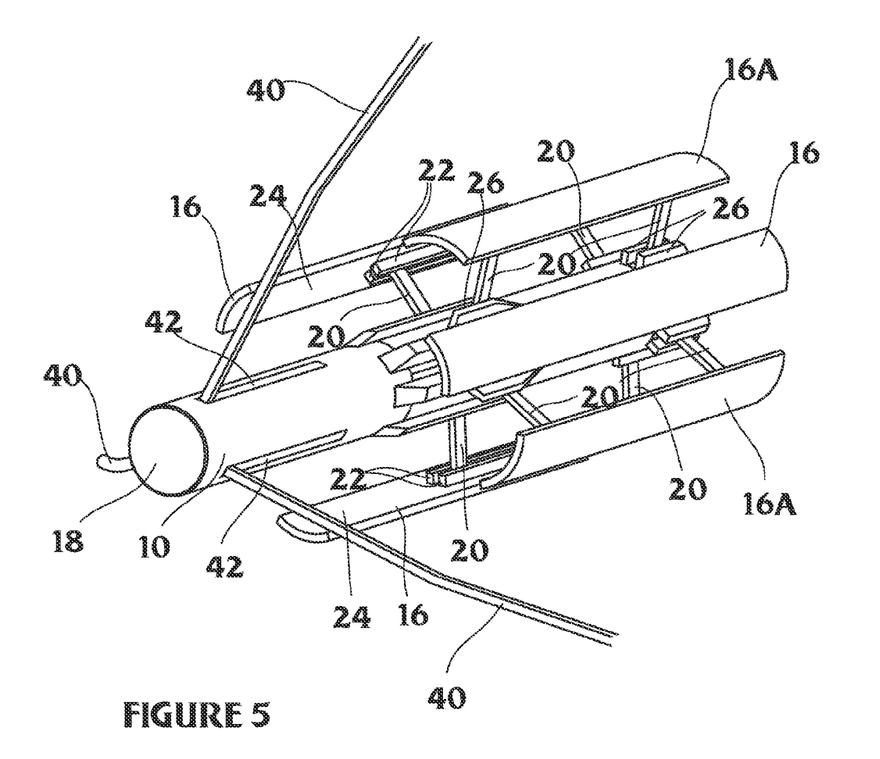
FIG. 5 is a perspective view of the body of the deployment device illustrated in FIG. 1 with the wings in an expanded position.

Movement of the sleeve (30) causes it to engage the end (28) of each strut (20) and move it in the same direction. This causes each strut (20) to pivot about the central hinge (26) with its end (23) moving in the opposite direction. In this way, the support surfaces (16) can be displaced from a radially withdrawn delivery position in which they abut the body (10), as shown in FIG. 4, in a generally radial direction away from the body to an extended position as shown in FIG. 5. Moving the sleeve (30) in the opposite direction causes the support surfaces (20) to move back into the radially withdrawn delivery position.

Three elongate locator arms (40) extend from the body (10) adjacent the end (18). The arms (40) each extend through a slot (42) in the body (10) and are evenly spaced about its circumference. The arms (40) are curved in their length with one end (44) hingedly secured to a rod (46) running within the sleeve (30) in the body. The tip (48) of each arm (40) is slightly enlarged and rounded. A collar (50) is provided over the rod (46) intermediate the arms (40) and the sleeve (30). A cable (52) running in the catheter (14) enables operation of the rod (46) by sliding axially within the sleeve (30). Operating the rod (46) to move in the direction of the end (12) of the body (10) causes the arms (40) to engage the collar (50) and pivot so that the tips (48) move in an arc away from the body (10). This causes symmetrical deployment of the arms (40) from a stowed condition in which they extend slightly away from the body (10) and then generally along the length the stent (2), to a deployed condition in which they extend in an umbrella-like fashion generally outwardly from the body (10). Movement of the rod in the opposite direction causes the arms (40) to engage the ends of the respective slots (42) and to move back into the stowed condition.

Figure 6:
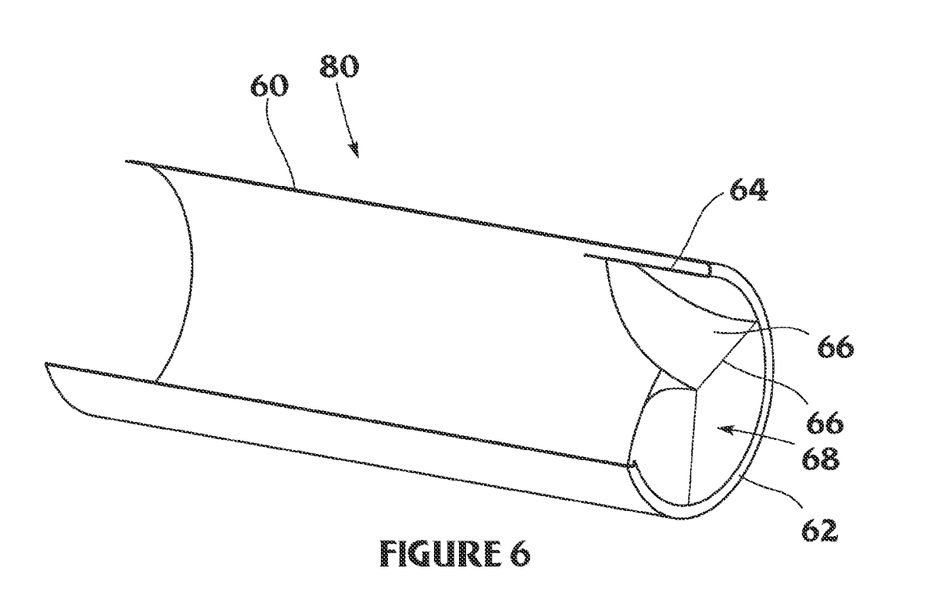
FIG. 6 is a part sectional perspective view of the membrane of the deployment device illustrated in FIG. 1 and showing the temporary valve therein.

Referring also to FIG. 6, a tubular membrane (60) extends over the wings (16). It is inwardly folded at one end (62) with the folded section (64) extending beneath the wings (16) adjacent the end (18) of the body (10). Three valve leaflets (66) are secured within the folded section (64). These form a temporary valve (68) which mimics a natural heart valve in its construction and operation in the same way as that in the stent and need not be described in further detail. The membrane (60) and valve leaflets (66) are made of a flexible plastics material including but not limited to polyethylene terephthalate (PET), polyamide, polyurethane, polytetrafluoroethylene (PTFE), polypropylene (PP), polyethylene (PE).

The shorter wings (16A) are the same length as the stent (2), while the remaining, longer wings support the folded section (64) of the membrane (60) and the temporary valve (68).

Figure 7:
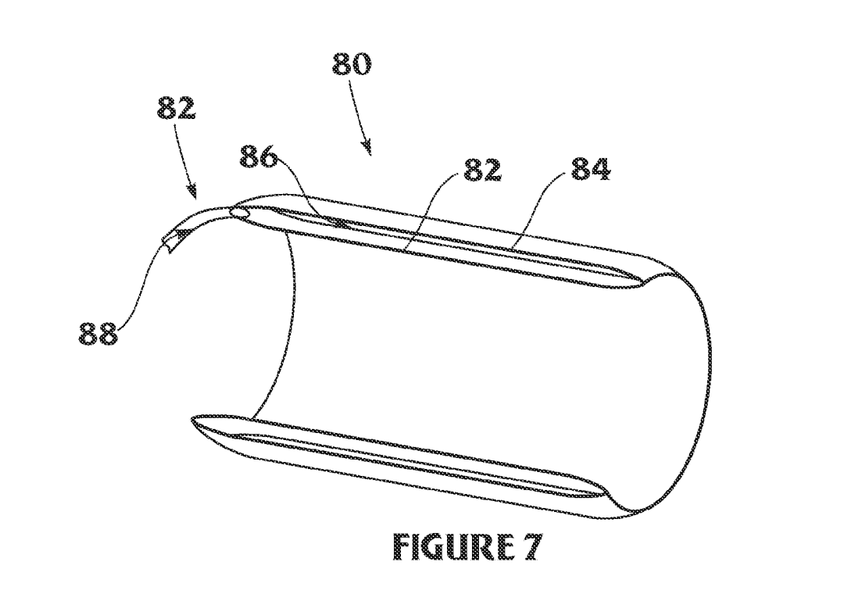
FIG. 7 is a part sectional perspective view of the annular balloon of the deployment device illustrated in FIG. 1.

Referring also to FIG. 7, an elongate annular balloon (80) is provided over the membrane (60). The balloon (80) thus has an inner side (82) which abuts the membrane (60) and an outer side (84) which abuts the stent (2). A cavity (86) is defined between the sides (82, 84) and is connected to an external source of fluid pressure (not shown) through a tube (88) associated with the catheter (14).

Figure 8:
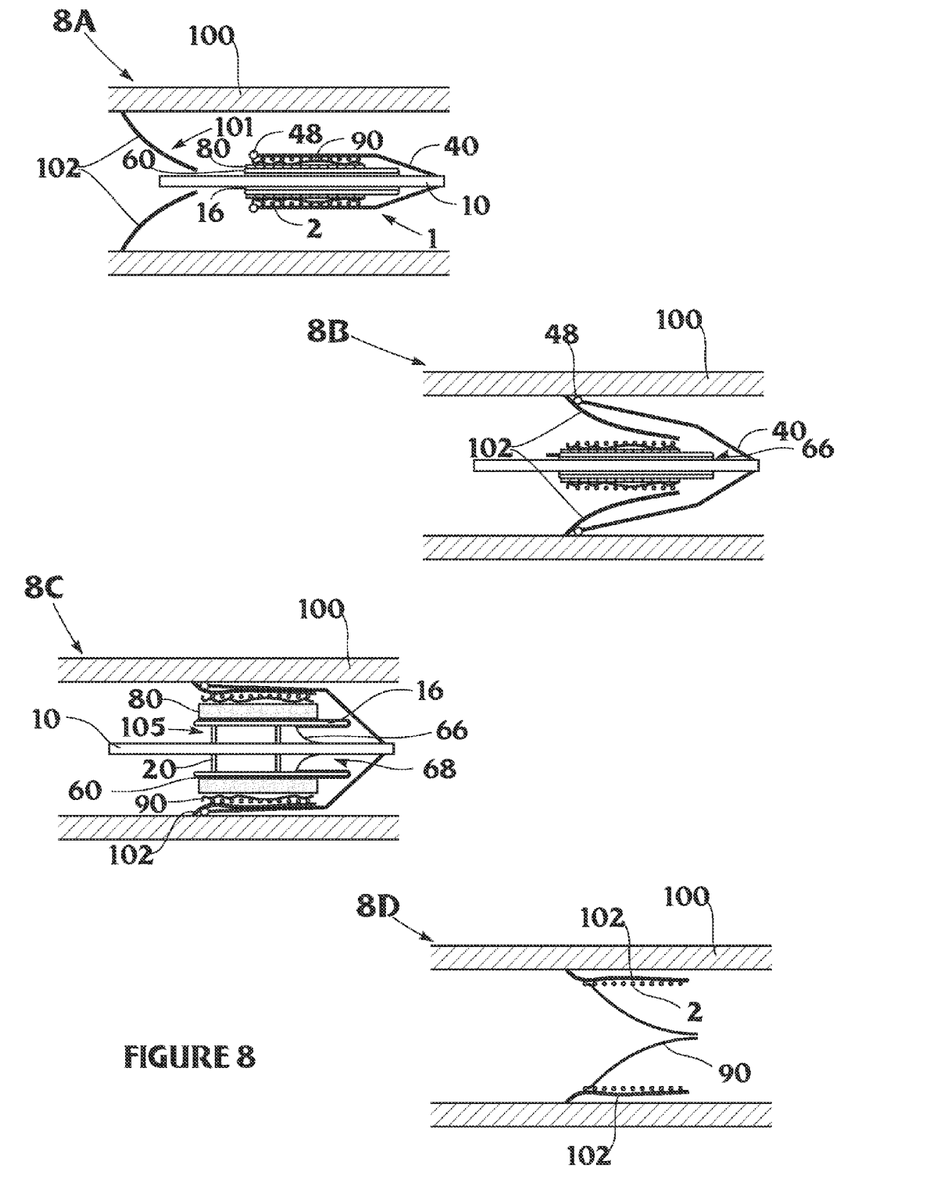
FIGS. 8A-D are part sectional side elevations illustrating progressive stages during the use of the stent deployment device illustrated in FIG. 1.

FIGS. 8A to 8D schematically illustrate the progressive use of the deployment device (1). With the stent (2) carrying the replacement valve (90) crimped over the deployment device and the locator arms (40) stowed over the stent (2), the assembly is passed through the apex of the heart into the aortic root (100) to a point distal to the aortic valve (101) so that the locator arms (40) may be deployed without interference from the aortic valve (101). Hereafter the locator arms (40) are deployed and the device is then retracted so that the locator arms (40) engage and seat of the bottom of the natural aortic valve leaflets (102) as shown in FIG. 8B. The enlarged rounded tips (48) of the locator arms (40) assist in preventing damage to the surrounding tissue during positioning of the locator arms. Also, the locator arms (40) are provided with a degree of flexibility to limit the outward force exerted by the tips (48) on the surrounding tissue. The locator arms (40) thus aid orientation, making slow and precise positioning possible under simple fluoroscopy or with sonography only With the device (1) located within the aortic valve (101) between the natural valve leaflets (102) the wings (16) are operated and moved to their expanded position. This causes an initial expansion of the stent (2) as well as ther opening of a flow passage (105) defined between the body (10) and membrane (60) and through which blood can flow as the heart (100) beats.

The temporary valve (68) provided within the passage (105) by the leaflets (66) permits flow of blood in substantially one direction only thus providing a temporary heart valve during deployment of the stent (2). By folding the membrane (60) as described above the temporary valve is supported against collapse during diastole.

Partial expansion of the stent (2) by the wings (16) also serves to pre-dilate the natural heart valve, should it be necessary.

Hereafter, the balloon (80) is inflated to cause final expansion of the stent (2). The membrane (60) assists in limiting inward expansion of the inner side (82) between the wings (16) and ensures that expansion of the balloon (80) takes place substantially outwardly. Once fully expanded, the stent (2) becomes secured in position within the natural aortic valve (101). The balloon (80) is subsequently deflated and the wings (16) retracted to the delivery position. Hereafter the device (1) is distally displaced until the locator arms (40) are free of the stent (2). The locator arms (40) are then moved to the stowed condition and the device (1) retracted from the aortic route and apex of the heart (100) leaving the stent (2) and replacement valve (90) in position as shown in FIG. 8D.

The stent deployment device of the invention will typically be supplied with a stent already pre-crimped over the wings and, where present, annular balloon, with the wings in their retracted delivery positions. It is envisaged that the stent deployment device of the invention may be reusable and will therefore be provided with another stent pre-crimped onto it at a suitable processing centre. The stent itself may carry a replacement heart valve, or may carry an endovascular graft.

The stent deployment device of the invention provides a number of significant advantages over the prior art. By creating a central flow path while expanding the balloon, no occlusion of the heart valve occurs and no sophisticated electro-stimulations are required to suppress cardiac output when using the deployment device while the internal valve prevents free regurgitation through the orifice during the filling phase of the heart (diastole) and normal haemodynamics and coronary perfusion are provided.

This enables a clinician to dilate the native heart valve and place the catheter-delivered prosthetic replacement heart valve without time limitations and without the need for sophisticated equipment in the operating room and significant support teams. Also, the locator arms permit the device to be accurately positioned without the need for costly imaging equipment and procedures.

The device thus has the potential of making available off pump heart valve replacements to millions of patients in the developing world who have no access to open heart surgery. It also holds advantages for patients in the developed world who fall within the small group of largely inoperable patients whose only hope is catheter based heart valve replacements. Also, eliminating outflow obstruction not only removes a compromising step for the patient's circulation but also allows a more precise placement of the stent based heart valve due to the lack of time constraints.

It will be appreciated, however, that many other embodiments of a deployment device exist which fall within the scope of the invention, especially as regards the configuration and operation thereof. For example, the wings can have any suitable shape and can be operable to expand a stent secured around the device in any suitable manner. For example, the struts may be hydraulically extendable. Indeed, the entire expansion means could be of an alternative construction and may be devoid of the struts described above.

Also, whereas the use of the balloon to cause final expansion of the stent is considered to provide a more uniform final expansion of the stent than the wings alone, it is foreseeable that the wings could be used to provide complete expansion of the stent without a balloon. Should a pre-dilatation of the valve not be necessary due to the fact that the valve suffers from pure incompetence, with no element of stenosis present, the expansion of the stent by the wings only is particularly possible.

Also, the locator arms can have any suitable shape and construction and could be operable in any suitable manner.

The membrane over the elongate surfaces is not strictly required but does assist in defining the flow path between the elongate surfaces and the body of the device and in limiting expansion of the balloon between the wings. If desired, the membrane can be secured to the elongate surfaces, including by way of adhesive or through pockets which fit over the ends of the wings. Also, any suitable temporary valve type and configuration can be used internally of the wings to provide a temporary valve during deployment of the stent.

The device can also be associated with any other suitable equipment, such as visual imaging devices, if desired. Also, an external tubular sheath may be employed to cover the device during insertion and retraction.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

The invention claimed is:

1. A stent deployment system comprising a stent and a stent deployment device, wherein the stent is secured over the stent deployment device for the purpose of delivery into an operative position in a human body, the device comprising a plurality of elongate wings, each of which has a length consistent with the length of the stent to be deployed using the deployment device, wherein the wings are arranged circumferentially about a central body which extends from, and is operable through, a catheter; the wings being movable between a radially withdrawn delivery position and expanded positions in which they are displaced radially outwards of the body and operable with sufficient force to cause at least partial expansion of the stent carried by the device during movement from the delivery position to an expanded position, and wherein a flow path is defined internally of the wings in the expanded positions thereof, and wherein a temporary valve is provided in such flow path to permit flow of blood though the flow path predominantly in one direction.

2. A stent deployment system as claimed in claim 1 wherein an annular balloon is provided over the wings, the balloon being inflatable to expand circumferentially to cause expansion of the stent secured thereover.

3. A stent deployment system as claimed in claim 1 wherein a plurality of elongate locator arms is secured to the body so as to be deployable from a stowed condition to an operative condition in which they are able to engage within a natural heart valve to locate the body within the natural heart valve.

4. A stent deployment system as claimed in claim 3 wherein the locator arms are curved in their length and are flexible with respect to the body.

5. A stent deployment system as claimed in claim 3 wherein the locator arms are hingedly secured to the body at or near one end thereof.

6. A stent deployment system as claimed in claim 1 wherein the flow path is defined at least in part by a membrane spanning the wings.

7. A stent deployment system as claimed in claim 6 wherein the membrane is tubular and carries the temporary valve internally thereof.

8. A stent deployment system as claimed in claim 1 wherein the wings are moved through struts pivotally secured to the body and operable between a stowed condition in which they extend generally in the direction of the length of the body, and an extended condition in which they extend in a generally radial direction from the body.

9. A stent deployment system as claimed in claim 8 wherein the struts are pivotally attached to the body intermediate their ends, to the wings at one extremity of each strut, and to an axially movable sleeve internally of the body at the other extremity of each strut.

10. A stent deployment system as claimed in claim 1 wherein the wings expand in a generally radial direction from the body.

11. A stent deployment system as claimed in claim 1 wherein the stent is pre-crimped over the wings and, where appropriate, annular expansion balloon, with the wings in a radially withdrawn delivery position.

12. A stent deployment system as claimed in claim 11 wherein the stent supports a replacement heart valve.

13. A stent deployment system as claimed in claim 11 wherein the stent supports an endovascular graft.

* * * * *

UNITED STATES PATENT AND TRADEMARK OFFICE
CERTIFICATE OF CORRECTION

PATENT NO. : 8,702,782 B2
APPLICATION NO. : 13/123380
DATED : April 22, 2014
INVENTOR(S) : Peter Paul Zilla, Deon Bezuidenhout and David Franklyn Williams It is certified that error appears in the above-identified patent and that said Letters Patent is hereby corrected as shown below:

On the Title Page, Item (73)

The name of the Assignee is corrected from STRAIT ACCESS TECHNOLOGIES HOLDINGS (PTY) LIMITED to STRAIT ACCESS TECHNOLOGIES (PTY) LIMITED.

Signed and Sealed this
Twenty-first Day of April, 2015

Michelle K. Lee
*Director of the United States Patent and Trademark Office*

UNITED STATES PATENT AND TRADEMARK OFFICE
CERTIFICATE OF CORRECTION

PATENT NO.       : 8,702,782 B2
APPLICATION NO.  : 13/123380
DATED            : April 22, 2014
INVENTOR(S)      : Zilla et al.

It is certified that error appears in the above-identified patent and that said Letters Patent is hereby corrected as shown below:

This certificate supersedes the Certificate of Correction issued April 21, 2015. The certificate is vacated since petition to correct assignee under 3.81 (b) was not acted on by the Office of Petitions. The Certificate of Correction was published in error and should not be issued.

Signed and Sealed this
Twenty-first Day of July, 2015

Michelle K. Lee
*Director of the United States Patent and Trademark Office*